(12) United States Patent
Benton

(10) Patent No.: US 12,178,700 B2
(45) Date of Patent: Dec. 31, 2024

(54) METHOD FOR DIRECTING CELLULAR MIGRATION PATTERNS ON A BIOLOGICAL TISSUE

(71) Applicant: Edwards Lifesciences Corporation, Irvine, CA (US)

(72) Inventor: Julie A. Benton, Mission Viejo, CA (US)

(73) Assignee: EDWARDS LIFESCIENCES CORPORATION, Irvine, CA (US)

(*) Notice: Subject to any disclaimer, the term of this patent is extended or adjusted under 35 U.S.C. 154(b) by 288 days.

(21) Appl. No.: 17/216,406

(22) Filed: Mar. 29, 2021

(65) Prior Publication Data

US 2021/0212818 A1 Jul. 15, 2021

Related U.S. Application Data

(63) Continuation of application No. 14/495,621, filed on Sep. 24, 2014, now Pat. No. 10,959,839.
(Continued)

(51) Int. Cl.
*A61F 2/00* (2006.01)
*A61F 2/24* (2006.01)
(Continued)

(52) U.S. Cl.
CPC .......... *A61F 2/2415* (2013.01); *A61F 2/2412* (2013.01); *A61L 27/3625* (2013.01);
(Continued)

(58) Field of Classification Search
None
See application file for complete search history.

(56) References Cited

U.S. PATENT DOCUMENTS 2,393,580 A 1/1946 Weiskopf
4,120,649 A 10/1978 Schechter
(Continued)

FOREIGN PATENT DOCUMENTS

CN 106390202 A 2/2017
EP 0169259 A1 1/1986
(Continued)

OTHER PUBLICATIONS

Carpentier, A., et al., "Biological Factors Affecting Long-Term Results of Valvular Heterografts," Forty-ninth Meeting of the American Association for Thoracic Surgery, San Francisco, CA, Mar. 31-Apr. 2, 1969.
(Continued)

*Primary Examiner* — Ann Schillinger
(74) *Attorney, Agent, or Firm* — Darren M. Franklin; Nathan Lee; Sheppard, Mullin, Richter & Hampton LLP

(57) ABSTRACT

A contoured biological tissue for a bioprostheses, such as a cardiac/vascular patch or a bioprosthetic heart valve, and methods of contouring the tissue, are described. A predetermined pattern is provided on the tissue, comprising a plurality of ridges or depressions that are configured to facilitate cellular migration in a first direction and discourage cellular migration in a second direction. The biological tissue can be used in connection with a bioprosthetic heart valve comprising a biological tissue leaflet structure coupled to a supporting frame.

19 Claims, 4 Drawing Sheets

Related U.S. Application Data

(60) Provisional application No. 61/888,080, filed on Oct. 8, 2013.

(51) Int. Cl.

| | | |
|---|---|---|
| *A61L 27/36* | (2006.01) | |
| *A61L 27/50* | (2006.01) | |
| *A61L 31/14* | (2006.01) | |
| *B23K 26/00* | (2014.01) | |
| *B23K 26/0622* | (2014.01) | |
| *B23K 26/082* | (2014.01) | |
| *B23K 26/352* | (2014.01) | |
| *B23K 103/00* | (2006.01) | |

(52) U.S. Cl.
CPC ....... *A61L 27/3683* (2013.01); *A61L 27/3691* (2013.01); *A61L 27/507* (2013.01); *B23K 26/0006* (2013.01); *B23K 26/0624* (2015.10); *B23K 26/082* (2015.10); *B23K 26/355* (2018.08); *A61F 2/0095* (2013.01); *A61F 2/2418* (2013.01); *A61F 2220/0075* (2013.01); *A61L 2430/20* (2013.01); *A61L 2430/40* (2013.01); *B23K 2103/32* (2018.08)

(56) References Cited

U.S. PATENT DOCUMENTS

| | | |
|---|---|---|
| 4,323,358 A | 4/1982 | Lentz et al. |
| 4,350,492 A | 9/1982 | Wright et al. |
| 4,372,743 A | 2/1983 | Lane |
| 4,378,224 A | 3/1983 | Nimni et al. |
| 4,402,697 A | 9/1983 | Pollock et al. |
| 4,405,327 A | 9/1983 | Pollock |
| 4,481,009 A | 11/1984 | Nashef |
| 4,553,974 A | 11/1985 | Dewanjee |
| 4,624,822 A | 11/1986 | Arru et al. |
| 4,647,283 A | 3/1987 | Carpentier et al. |
| 4,648,881 A | 3/1987 | Carpentier et al. |
| 4,758,151 A | 7/1988 | Arru et al. |
| 4,770,665 A | 9/1988 | Nashef |
| 4,776,853 A | 10/1988 | Klement et al. |
| 4,786,287 A | 11/1988 | Nashef et al. |
| 4,838,888 A | 6/1989 | Nashef |
| 4,865,871 A | 9/1989 | Livesey et al. |
| 4,885,005 A | 12/1989 | Nashef et al. |
| 4,958,008 A | 9/1990 | Petite et al. |
| 4,976,733 A | 12/1990 | Girardot |
| 5,002,566 A | 3/1991 | Carpentier et al. |
| 5,051,401 A | 9/1991 | Sikes |
| 5,080,670 A | 1/1992 | Imamura et al. |
| 5,094,661 A | 3/1992 | Levy et al. |
| 5,104,405 A | 4/1992 | Nimni |
| 5,116,564 A | 5/1992 | Jansen et al. |
| 5,147,514 A | 9/1992 | Mechanic |
| 5,154,007 A | 10/1992 | Piunno et al. |
| 5,200,399 A | 4/1993 | Wettlaufer et al. |
| 5,215,541 A | 6/1993 | Nashef et al. |
| 5,279,612 A | 1/1994 | Eberhardt |
| 5,329,846 A | 7/1994 | Bonutti |
| 5,397,353 A | 3/1995 | Oliver et al. |
| 5,437,287 A | 8/1995 | Phillips et al. |
| 5,447,536 A | 9/1995 | Girardot et al. |
| 5,460,962 A | 10/1995 | Kemp |
| 5,476,516 A | 12/1995 | Seifter et al. |
| 5,489,297 A * | 2/1996 | Duran ................... A61F 2/2418 623/2.13 |
| 5,509,932 A | 4/1996 | Keogh et al. |
| 5,558,875 A | 9/1996 | Wang |
| 5,595,571 A | 1/1997 | Jaffe et al. |
| 5,613,982 A | 3/1997 | Goldstein |
| 5,645,587 A | 7/1997 | Chanda et al. |
| 5,674,298 A | 10/1997 | Levy et al. |
| 5,697,972 A | 12/1997 | Kim et al. |
| 5,713,953 A | 2/1998 | Vallana et al. |
| 5,720,777 A | 2/1998 | Jaffe et al. |
| 5,720,894 A | 2/1998 | Neev et al. |
| 5,733,339 A | 3/1998 | Girardot et al. |
| 5,746,775 A | 5/1998 | Levy et al. |
| 5,766,520 A | 6/1998 | Bronshtein |
| 5,769,780 A | 6/1998 | Hata et al. |
| 5,782,914 A | 7/1998 | Schankereli |
| 5,782,931 A | 7/1998 | Yang et al. |
| 5,843,180 A | 12/1998 | Jaffe et al. |
| 5,843,181 A | 12/1998 | Jaffe et al. |
| 5,855,620 A | 1/1999 | Bishopric et al. |
| 5,861,028 A | 1/1999 | Angell |
| 5,862,806 A | 1/1999 | Cheung |
| 5,873,812 A | 2/1999 | Ciana et al. |
| 5,899,936 A | 5/1999 | Goldstein |
| 5,910,170 A * | 6/1999 | Reimink ............... A61F 2/2418 623/2.38 |
| 5,911,951 A | 6/1999 | Girardot et al. |
| 5,919,472 A | 7/1999 | Trescony et al. |
| 5,921,980 A | 7/1999 | Kirn |
| 5,931,969 A | 8/1999 | Carpentier et al. |
| 5,935,168 A | 8/1999 | Yang et al. |
| 5,945,319 A | 8/1999 | Keogh |
| 5,961,549 A * | 10/1999 | Nguyen ................ A61F 2/2415 623/2.12 |
| 5,977,153 A | 11/1999 | Camiener |
| 5,993,844 A | 11/1999 | Abraham et al. |
| 6,008,292 A | 12/1999 | Lee et al. |
| 6,017,741 A | 1/2000 | Keogh |
| 6,093,530 A | 7/2000 | McIlroy et al. |
| 6,106,555 A | 8/2000 | Yang |
| 6,117,979 A | 9/2000 | Hendriks et al. |
| 6,121,041 A | 9/2000 | Mirsch, II et al. |
| 6,132,472 A | 10/2000 | Bonutti |
| 6,132,473 A | 10/2000 | Williams et al. |
| 6,132,986 A | 10/2000 | Pathak et al. |
| 6,156,030 A | 12/2000 | Neev |
| 6,156,531 A | 12/2000 | Pathak et al. |
| 6,165,215 A | 12/2000 | Rottenberg et al. |
| 6,166,184 A | 12/2000 | Hendriks et al. |
| 6,171,335 B1 | 1/2001 | Wheatley et al. |
| 6,174,331 B1 | 1/2001 | Moe et al. |
| 6,177,514 B1 | 1/2001 | Pathak et al. |
| 6,190,407 B1 | 2/2001 | Ogle et al. |
| 6,193,749 B1 | 2/2001 | Schroeder et al. |
| 6,203,755 B1 | 3/2001 | Odland |
| 6,206,917 B1 | 3/2001 | Williams et al. |
| 6,210,957 B1 | 4/2001 | Carpentier et al. |
| 6,214,054 B1 | 4/2001 | Cunanan et al. |
| 6,214,055 B1 * | 4/2001 | Simionescu ........ A61L 27/3687 623/23.72 |
| 6,231,608 B1 | 5/2001 | Stone |
| 6,231,614 B1 | 5/2001 | Yang |
| 6,251,579 B1 | 6/2001 | Moore et al. |
| 6,254,635 B1 | 7/2001 | Schroeder et al. |
| 6,267,786 B1 | 7/2001 | Stone |
| 6,277,555 B1 | 8/2001 | Duran et al. |
| 6,287,338 B1 | 9/2001 | Sarnowski et al. |
| 6,293,970 B1 | 9/2001 | Wolfinbarger, Jr. et al. |
| 6,302,909 B1 | 10/2001 | Ogle et al. |
| 6,312,474 B1 | 11/2001 | Francis et al. |
| 6,322,593 B1 | 11/2001 | Pathak et al. |
| 6,328,762 B1 | 12/2001 | Anderson et al. |
| 6,334,873 B1 | 1/2002 | Lane et al. |
| 6,352,708 B1 | 3/2002 | Duran et al. |
| 6,364,905 B1 | 4/2002 | Simpson et al. |
| 6,375,680 B1 | 4/2002 | Carlyle |
| 6,383,732 B1 | 5/2002 | Stone |
| 6,391,538 B1 | 5/2002 | Vyavahare et al. |
| 6,394,096 B1 | 5/2002 | Constantz |
| 6,448,076 B2 | 9/2002 | Dennis et al. |
| 6,468,660 B2 | 10/2002 | Ogle et al. |
| 6,471,723 B1 | 10/2002 | Ashworth et al. |
| 6,479,079 B1 | 11/2002 | Pathak et al. |
| 6,482,199 B1 | 11/2002 | Neev |
| 6,506,339 B1 | 1/2003 | Girardot et al. |
| 6,509,145 B1 | 1/2003 | Torrianni |
| 6,534,004 B2 | 3/2003 | Chen et al. |

(56) References Cited

U.S. PATENT DOCUMENTS

| | | | |
|---|---|---|---|
| 6,547,827 B2 | 4/2003 | Carpentier et al. | |
| 6,561,970 B1 | 5/2003 | Carpentier et al. | |
| 6,569,200 B2 | 5/2003 | Wolfinbarger, Jr. et al. | |
| 6,582,464 B2 | 6/2003 | Gabbay | |
| 6,589,591 B1 | 7/2003 | Mansouri et al. | |
| 6,605,667 B1 | 8/2003 | Badejo et al. | |
| 6,617,142 B2 | 9/2003 | Keogh et al. | |
| 6,630,001 B2 | 10/2003 | Duran et al. | |
| 6,652,594 B2 | 11/2003 | Francis et al. | |
| 6,653,062 B1 | 11/2003 | DePablo et al. | |
| 6,682,559 B2 | 1/2004 | Myers et al. | |
| 6,696,074 B2 | 2/2004 | Dai et al. | |
| 6,734,018 B2 | 5/2004 | Wolfinbarger, Jr. et al. | |
| 6,753,181 B2 | 6/2004 | Atala | |
| 6,790,229 B1 | 9/2004 | Berreklouw | |
| 6,797,000 B2 | 9/2004 | Simpson et al. | |
| 6,872,226 B2 | 3/2005 | Cali et al. | |
| 6,878,168 B2 | 4/2005 | Carpentier et al. | |
| 6,908,591 B2 | 6/2005 | MacPhee et al. | |
| 6,911,043 B2 | 6/2005 | Myers et al. | |
| 6,919,172 B2 | 7/2005 | DePablo et al. | |
| 7,008,763 B2 | 3/2006 | Cheung | |
| 7,029,434 B2 | 4/2006 | Carpentier et al. | |
| 7,037,333 B2 | 5/2006 | Myers et al. | |
| 7,063,726 B2 | 6/2006 | Crouch et al. | |
| 7,078,163 B2 | 7/2006 | Torrianni | |
| 7,141,064 B2 | 11/2006 | Scott et al. | |
| 7,143,769 B2 | 12/2006 | Stoltz et al. | |
| 7,214,344 B2 | 5/2007 | Carpentier et al. | |
| 7,238,200 B2 | 7/2007 | Lee et al. | |
| 7,318,998 B2 | 1/2008 | Goldstein et al. | |
| 7,338,757 B2 | 3/2008 | Wolfinbarger, Jr. et al. | |
| 7,354,749 B2 | 4/2008 | Fisher et al. | |
| 7,367,969 B2 | 5/2008 | Stoltz et al. | |
| RE40,570 E | 11/2008 | Carpentier et al. | |
| 7,498,565 B2 | 3/2009 | Silberberg et al. | |
| 7,550,152 B2 * | 6/2009 | Pandit | A61L 27/3687 424/551 |
| 7,566,343 B2 * | 7/2009 | Jenson | A61F 2/2412 623/2.38 |
| 7,579,381 B2 | 8/2009 | Dove | |
| 7,594,974 B2 | 9/2009 | Cali et al. | |
| 7,648,676 B2 | 1/2010 | Mills et al. | |
| 7,682,304 B2 | 3/2010 | Heyninck-Jantz et al. | |
| 7,722,666 B2 * | 5/2010 | Lafontaine | A61F 2/2436 623/2.11 |
| 7,901,461 B2 * | 3/2011 | Harmon | A61L 27/38 623/23.72 |
| 7,914,569 B2 | 3/2011 | Nguyen et al. | |
| 7,919,112 B2 | 4/2011 | Pathak et al. | |
| 7,972,376 B1 | 7/2011 | Dove et al. | |
| 8,007,992 B2 | 8/2011 | Tian et al. | |
| 8,038,708 B2 | 10/2011 | Case et al. | |
| 8,043,450 B2 | 10/2011 | Cali et al. | |
| 8,075,615 B2 | 12/2011 | Eberhardt et al. | |
| 8,105,375 B2 | 1/2012 | Navia et al. | |
| 8,136,218 B2 | 3/2012 | Millwee et al. | |
| 8,308,797 B2 | 11/2012 | Paniagua et al. | |
| 8,361,144 B2 | 1/2013 | Fish et al. | |
| 8,377,143 B2 | 2/2013 | Hamby et al. | |
| 8,475,827 B2 | 7/2013 | Hamby et al. | |
| 8,657,881 B2 * | 2/2014 | Kladakis | A61F 2/3872 623/14.12 |
| 9,107,739 B2 | 8/2015 | Lelkes et al. | |
| 9,994,812 B2 * | 6/2018 | Kim | C12M 25/14 |
| 10,383,978 B2 | 8/2019 | Dong et al. | |
| 10,722,613 B2 | 7/2020 | Ashworth et al. | |
| 10,959,839 B2 * | 3/2021 | Benton | B23K 26/355 |
| 2001/0000804 A1 | 5/2001 | Goldstein et al. | |
| 2001/0025196 A1 | 9/2001 | Chinn et al. | |
| 2001/0027344 A1 | 10/2001 | Bonutti | |
| 2001/0032024 A1 | 10/2001 | Cunanan et al. | |
| 2001/0039459 A1 | 11/2001 | Stone | |
| 2002/0001834 A1 | 1/2002 | Keogh et al. | |
| 2002/0051806 A1 * | 5/2002 | Mallapragada | A61L 27/56 435/368 |
| 2002/0091441 A1 | 7/2002 | Guzik | |
| 2002/0111532 A1 | 8/2002 | Pathak et al. | |
| 2002/0173842 A1 * | 11/2002 | Buchanan | A61F 2/2409 623/2.14 |
| 2002/0183844 A1 | 12/2002 | Fishman et al. | |
| 2003/0035843 A1 | 2/2003 | Livesey et al. | |
| 2003/0055496 A1 | 3/2003 | Cai et al. | |
| 2003/0069635 A1 * | 4/2003 | Cartledge | A61F 2/2412 623/2.12 |
| 2003/0078652 A1 * | 4/2003 | Sutherland | A61F 2/2412 623/2.12 |
| 2003/0093147 A1 * | 5/2003 | Ogle | A61L 27/54 623/2.12 |
| 2003/0125805 A1 | 7/2003 | Johnson et al. | |
| 2003/0135284 A1 | 7/2003 | Crouch et al. | |
| 2003/0167089 A1 | 9/2003 | Lane | |
| 2003/0212454 A1 | 11/2003 | Scott et al. | |
| 2003/0229394 A1 * | 12/2003 | Ogle | A61L 27/3691 623/2.14 |
| 2004/0030381 A1 | 2/2004 | Shu | |
| 2004/0086543 A1 | 5/2004 | Keogh et al. | |
| 2004/0158320 A1 | 8/2004 | Simionescu et al. | |
| 2005/0010773 A1 | 1/2005 | Lapstun et al. | |
| 2005/0107870 A1 * | 5/2005 | Wang | B82Y 25/00 623/1.44 |
| 2005/0119736 A1 | 6/2005 | Zilla et al. | |
| 2005/0136510 A1 | 6/2005 | Hendriks et al. | |
| 2005/0211680 A1 | 9/2005 | Li et al. | |
| 2006/0084957 A1 | 4/2006 | Delfyett et al. | |
| 2006/0099326 A1 | 5/2006 | Keogh et al. | |
| 2006/0110370 A1 | 5/2006 | Pathak et al. | |
| 2006/0129216 A1 * | 6/2006 | Hastings | A61B 5/076 607/2 |
| 2006/0159641 A1 | 7/2006 | Girardot et al. | |
| 2006/0193885 A1 | 8/2006 | Leonard Neethling et al. | |
| 2006/0210960 A1 | 9/2006 | Livesey et al. | |
| 2006/0217804 A1 | 9/2006 | Dove | |
| 2006/0217805 A1 | 9/2006 | Dove | |
| 2006/0253192 A1 | 11/2006 | Atala et al. | |
| 2007/0050014 A1 | 3/2007 | Johnson | |
| 2007/0073392 A1 | 3/2007 | Heyninck-Jantz et al. | |
| 2007/0203576 A1 | 8/2007 | Lee et al. | |
| 2007/0233228 A1 | 10/2007 | Eberhardt et al. | |
| 2007/0254005 A1 * | 11/2007 | Pathak | A61P 31/00 424/423 |
| 2008/0302372 A1 | 12/2008 | Davidson et al. | |
| 2008/0319166 A1 | 12/2008 | Shen | |
| 2009/0041729 A1 | 2/2009 | Wolfinbarger, Jr. et al. | |
| 2009/0130162 A2 | 5/2009 | Pathak et al. | |
| 2009/0137999 A1 | 5/2009 | Silberberg et al. | |
| 2009/0188900 A1 | 7/2009 | Cali et al. | |
| 2009/0248145 A1 * | 10/2009 | Chan | C12N 5/0691 435/378 |
| 2009/0326524 A1 | 12/2009 | Cali et al. | |
| 2010/0036484 A1 | 2/2010 | Hariton et al. | |
| 2010/0047436 A1 | 2/2010 | Beith | |
| 2010/0254900 A1 * | 10/2010 | Campbell | A61P 29/00 424/9.4 |
| 2011/0015739 A1 | 1/2011 | Cheung et al. | |
| 2011/0029654 A1 | 2/2011 | Takeda et al. | |
| 2011/0081323 A1 * | 4/2011 | Kleinsek | A61P 43/00 514/20.7 |
| 2011/0092966 A1 | 4/2011 | Guo et al. | |
| 2011/0177150 A1 | 7/2011 | Pathak et al. | |
| 2011/0214398 A1 | 9/2011 | Liburd et al. | |
| 2011/0238167 A1 | 9/2011 | Dove et al. | |
| 2011/0293667 A1 * | 12/2011 | Baksh | C12N 5/0663 435/69.1 |
| 2011/0295363 A1 | 12/2011 | Girard et al. | |
| 2011/0300625 A1 | 12/2011 | Paniagua et al. | |
| 2011/0306124 A1 | 12/2011 | Strasly et al. | |
| 2011/0311493 A1 | 12/2011 | Dove et al. | |
| 2012/0035720 A1 | 2/2012 | Cali et al. | |
| 2012/0059487 A1 | 3/2012 | Cunanan et al. | |
| 2012/0067855 A1 | 3/2012 | Guo et al. | |
| 2012/0078356 A1 | 3/2012 | Fish et al. | |

(56) References Cited

U.S. PATENT DOCUMENTS

| | | | |
|---|---|---|---|
| 2012/0095551 A1 | 4/2012 | Navia et al. | |
| 2012/0109613 A1* | 5/2012 | Boyden | C07K 16/2809 |
| | | | 703/11 |
| 2012/0123557 A1 | 5/2012 | Carpentier et al. | |
| 2012/0185038 A1 | 7/2012 | Fish et al. | |
| 2012/0302467 A1 | 11/2012 | Levkin et al. | |
| 2012/0328905 A1 | 12/2012 | Guo et al. | |
| 2013/0018454 A1 | 1/2013 | Lelkes et al. | |
| 2013/0122583 A1 | 5/2013 | Neethling | |
| 2013/0238088 A1 | 9/2013 | Navia et al. | |
| 2013/0243738 A1 | 9/2013 | Griffiths et al. | |
| 2014/0005772 A1* | 1/2014 | Edelman | A61L 27/34 |
| | | | 29/890.12 |
| 2014/0093905 A1* | 4/2014 | Ingber | G01N 33/5005 |
| | | | 435/287.1 |
| 2014/0257472 A1* | 9/2014 | Kutty | A61F 2/2415 |
| | | | 264/28 |
| 2014/0288641 A1 | 9/2014 | Levy et al. | |
| 2014/0314992 A1 | 10/2014 | Palmaz et al. | |
| 2014/0370599 A1 | 12/2014 | Strasly et al. | |
| 2015/0088247 A1 | 3/2015 | L'Heureux et al. | |
| 2017/0173214 A1 | 6/2017 | Wang et al. | |
| 2019/0374680 A1 | 12/2019 | Lehenberger et al. | |
| 2022/0323508 A1* | 10/2022 | Peterson | A61L 27/3878 |

FOREIGN PATENT DOCUMENTS

| | | | | |
|---|---|---|---|---|
| EP | 2394673 | A1 | 12/2011 | |
| EP | 2907531 | A1 * | 8/2015 | A61F 2/0059 |
| WO | 8401894 | A1 | 5/1984 | |
| WO | 9511047 | A1 | 4/1995 | |
| WO | 9522361 | A1 | 8/1995 | |
| WO | 9534332 | A1 | 12/1995 | |
| WO | 9613227 | A1 | 5/1996 | |
| WO | 9807452 | A1 | 2/1998 | |
| WO | 9832400 | A1 | 7/1998 | |
| WO | 9843556 | A1 | 10/1998 | |
| WO | 9857604 | A1 | 12/1998 | |
| WO | 0032252 | A1 | 6/2000 | |
| WO | 2004082536 | A1 | 9/2004 | |
| WO | 2006026325 | A2 | 3/2006 | |
| WO | 2006099334 | A2 | 9/2006 | |
| WO | 2007016251 | A3 | 4/2008 | |
| WO | 2011119754 | A2 | 9/2011 | |
| WO | 2013009851 | A2 | 1/2013 | |

OTHER PUBLICATIONS

Chanda, J., et al., "Heparin in Calcification Prevention of Porcine Pericardial Bioprostheses," Biomaterials, Elsevier Science Publishers, vol. 18, No. 16, ISSN: 0142-9612, Aug. 1, 1997.

Chvapil, M., et al., "Use of Chemically Purified And Cross-Linked Bovine Pericardium As A Ligament Substitute," Journal of Biomedical Materials Research, vol. 21, No. 12, pp. 1383-1394, 1987, University of Arizona Health Science Center, Tucson, AZ.

Dahm, Manfred, et al., "Effects of Surface Seeding with Vital Cells on the Calcium Uptake of Biological Materials for Heart Valve Replacement," J Heart Valve Dis, vol. 5, No. 2, Mar. 1996, 148-151.

Dalton, B.A., et al., "Modulation of epithlial tissue and cell migration by microgrooves," Journal of biomedical materials research, 2011, vol. 56, pp. 195-207.

Fahner, P., et al., "Systematic Review of Preservation Methods and Clinical Outcome of Infrainguinal Vascular Allografts," Journal of Vascular Surgery, vol. 44, No. 3, pp. 518-524, 2006.

Fumoto, H., et al., "Performance of Bioprosthetic Valves After Glycerol Dehydration, Ethylene Oxide Sterilization, and Rehydration," Innovations, vol. 6, No. 1, Jan./ Feb. 2011.

Grabenwoger, M. et al. "Decreased Tissue Reaction to Bioprosthetic Heart Valve Material after L-glutaimc acid Treatment. A Morphological Study." J. Biomed Mater. Res. Sep. 1992;26(9):1231-40.

Grant, R.A., et al., "The Effects of Irradiation with High Energy Electrons on the Structure and Reactivity of Native and Cross-Linked Collagen Fibres," J. Cell Sci. vol. 7, 99. 387-405, 1970.

Hauschka, P., et al., "Direct Identification of the Calcium—Binding Amino Acid, y-Carboxyglutamate, in Mineralized Tissue," Proc. Nat. Acad. Sci, vol. 72, No. 10, pp. 3925-3929, Oct. 1975.

Jayakrishnan, A., et al., "Glutaraldehyde as a Fixative in Bioprostheses and Drug Delivery Matrices," Biomaterials, vol. 17, Issue 5, 1996, pp. 471-484.

Khora, Eugene, "Methods for the Treatment of Collagenous Tissues for Bioprostheses," Biomaterials, vol. 18, Issue 2, Jan. 1997, pp. 95-105.

Liao, K., et al., "Mechanical Stress: An Independent Determinant of Early Bioprosthetic Calcification in Humans," Ann. Throac. Surg 2008;86:491-495.

Neethling, W, et al. Enhanced Biostability and Biocompatibility of Decellularized Bovine Pericardium, Crosslinked with an Ultra-Low Concentration Monomeric Aldehyde and Treated with Adapt®, J. Heart Valve Dis. 2008; 17:456-464.

Olde Damink, L.H.H., et al., "Influence of Ethylene Oxide Gas Treatment on the in vitro Degradation Behavior of dermal Sheep Collagen," Journal of Biomedical Materials Resarch, vol. 29, pp. 149-155, 1995.

R Parker, et al. Storage of Heart Valve Allografts in Glycerol With Subsequent Antibiotic Sterilisation, Thorax, 1978, 638-645, vol. 33:5, British Thoracic Society, London, UK.

Saegeman, V., et al., "Short and long term bacterial inhibiting effect of high concentrations of glycerol used in the prevention of skin allografts," Science Direct, Burns, No. 34, Mar. 2008.

Schmidt, C., et al., "Acellular Vascular Tissues: Natural Biomaterials for Tissue Repair and Tissue Engineering," Biomaterials, vol. 21, pp. 2215-2231, 2000.

Trantina-Yates AE, et al. "Detoxification of Top Enhanced, Diamine-Extended Glutaraldehyde Fixation Significantly Reduces Bioprosthetic Root Calcification in the Sheep Model," J. Heart Valve Dis. Jan. 2003; 12(1):93-100.

Uttayarat, P. et al., "Microtopography and flow modulate the direction of endothelial cell migration," American Journal of Physiology-Heart and Circulatory Physiology, 2008, vol. 294. pp. H1027-H1035.

Zilla, P., et al., "Carbodiimide Treatment Dramatically Potentiates the Anticalcific Effect of Alpha-Amino Oleic Acid on Glutaraldehyde-Fixed Aortic Wall Tissue," The Annals of Thoracic Surgery, Elsevier, vol. 79, No. 3, ISSN: 0003-4975; Mar. 1, 2005.

St. Jude Medical Scores with the FDA on Valves with Anti-Calcification Technology, Nov. 28, 2007, http://www.medgadget.com/2007/11/st_jude_medical_scores_with_the_fda_on_valves_with_anticalcification_technology.html.

Jamieson W.R. et al., St Jude Medical Epic Porcine Bioprosthesis: Results of The Regulatory Evaluation. J Thorac Cardiovasc Surg., Jan. 31, 2011, vol. 141, No. 6, pp. 1449-1454.

Jeon H. et al., "The Effect of Micronscale Anisotropic Cross Patterns on Fibroblast Migration", Biomaterials, Mar. 2, 2010, vol. 31, No. 15, pp. 4286-4295.

Isenberg B.C. et al., "A Thermoresponsive, Microtextured Substrate for Cell Sheet Engineering with Defined Structural Organization", Biomaterials, Jun. 1, 2009, vol. 29, No. 17, pp. 2565-2572.

* cited by examiner

METHOD FOR DIRECTING CELLULAR MIGRATION PATTERNS ON A BIOLOGICAL TISSUE

CROSS REFERENCE TO RELATED APPLICATIONS

This application is a continuation of U.S. patent application Ser. No. 14/495,621, filed Sep. 24, 2014, now, U.S. Pat. No. 10,959,839, which claims the benefit of U.S. Patent Application No. 61/888,080, filed Oct. 8, 2013, the entire disclosures all of which are incorporated by reference for all purposes.

FIELD OF THE INVENTION

The invention relates to a method of treating biological tissue and, more particularly, to a method for imparting topographical changes onto a surface of a bioprosthetic tissue to direct or control patterns of cellular migration and tissue formation on the tissue.

BACKGROUND

Biological tissue, such as animal pericardium (e.g., bovine, porcine), has come into common use in connection with medical devices and implantable bioprostheses, such as bioprosthetic heart valves and vascular patches. The use of biological tissue in implanted bioprostheses, however, is not without its complications. Once implanted in the body, the biological tissue may become calcified or may stimulate the formation of scar or other types of tissue, such as pannus. The biological tissue may also stimulate cells to migrate into and integrate the implanted biological tissue into the host body.

One of the more serious complications associated with the implantation of prosthetic heart valves incorporating biological tissue is obstructive valve failure caused by pannus formation. Pannus is a membrane of granulation tissue, rich in fibroblasts, that forms in response to healing. The body may produce pannus where the native valve has been removed and a prosthetic heart valve has been implanted.

In many cases, pannus growth does not encroach the valve orifice or chamber space, but occasionally the hanging edges can hit or obstruct a leaflet. When pannus overgrowth interferes with valve functioning, surgery is the only option to remove the pannus overgrowth. There is no reliable way of predicting whether a particular patient will be more or less susceptible to pannus overgrowth.

Pannus overgrowth is estimated to be the cause of obstructive heart valve failure in a significant number of cases. In the aortic position, pannus formation occurs mainly on the inflow or ventricular side, while in the mitral position, it occurs both on the atrial and ventricular sides. In order to prevent tissue ingrowth into the clearance of leaflets, prosthetic valves have been designed with longer housing cylinders with the goal of creating an ingrowth barrier. Such valve designs, however, are often impractical, infeasible or undesirable for minimally-invasive or percutaneously-deliverable heart valves, as an important design goal for such valves is to reduce the delivery profile as much as practically possible. Thus, the inclusion of additional features or structures which add to the material bulk of the valves is generally avoided.

What is therefore needed are bioprosthetic heart valves which control pannus formation or which reduce or eliminate the likelihood of pannus overgrowth that interferes with proper valve functioning.

BRIEF SUMMARY

A contoured biological tissue for a bioprostheses, such as a cardiac/vascular patch or a bioprosthetic heart valve, and methods of preparing the contoured tissue, are described herein. A predetermined pattern is provided on the tissue, comprising a plurality of ridges or depressions that are configured to facilitate cellular migration in a first direction and discourage cellular migration in a second direction. The biological tissue can be used in connection with a bioprosthetic heart valve comprising a biological tissue leaflet structure coupled to a supporting frame.

In one embodiment, a method for manufacturing a bioprosthetic heart valve is described. The method comprises contouring a portion of a biological tissue valve leaflet with a predetermined pattern. The predetermined pattern comprises a plurality of ridges or depressions oriented in the same or different directions. Adjacent ridges or depressions are at least 10 microns apart to prevent or at least impede the migration of fibroblasts transversely across the ridges or depressions. The contouring can be performed with a laser, preferably a femtosecond laser.

The biological tissue can be at least partially crosslinked, and/or at least partially dehydrated, such as with a glycerin-based treatment solution, before the contouring. The biological tissue can be treated with a capping agent after the crosslinking, after the contouring, or both.

The method can further comprise packaging the bioprosthetic heart valve in a package that does not contain a liquid storage solution in contact with the bioprosthetic heart valve.

In another embodiment, a contoured bioprosthetic heart valve is described. The contoured bioprosthetic heart valve comprises one or a plurality of leaflets formed from a biological tissue and a contoured pattern is provided on the leaflets. The contoured pattern comprises a plurality of ridges or depressions, the distance between adjacent ridges or depressions being at least 10 microns. The plurality of ridges or depressions can comprise a first set of parallel depressions or ridges, and can further comprise a second set of parallel ridges or grooves transversing the first set of parallel ridges or grooves at an angle.

The bioprosthetic heart valve can further comprise sutures coupling the one or more leaflets to a support structure or a skirt. The predetermined pattern can be disposed on the leaflets adjacent to at least a portion of the sutures. The one or plurality of heart valve leaflets can each comprise a straight free edge and an arcuate cusp edge and the contoured pattern is provided substantially along the arcuate cusp edge.

In a further embodiment, a contoured bioprosthetic heart valve for implantation within an arterial wall of a patient is described. The contoured bioprosthetic heart valve comprises a biological tissue leaflet structure coupled to a supporting frame. The biological tissue leaflet structure has a circumferential outer peripheral surface facing the arterial wall. A contoured pattern is provided around the circumferential outer peripheral surface. The contoured pattern comprises a plurality of ridges or depressions, spaced and/or sized to prevent or impede cellular migration across the ridges or depressions. The adjacent ridges or depressions are preferably at least 10 microns apart. The contoured pattern can be provided along an entire length of sutures coupling the biological tissue leaflet structure to the supporting frame.

In yet a further embodiment, a contoured bioprosthetic heart valve is described. The contoured bioprosthetic heart valve comprises one or a plurality of leaflets formed from a biological tissue. The leaflets each comprise a straight free edge and an arcuate cusp edge. A contoured pattern is provided on the leaflets. The contoured pattern comprises a plurality of ridges or depressions extending radially from the straight free edge to the arcuate cusp edge. Cellular migration is promoted along the ridges or depressions.

In still another embodiment, a method for treating a biological tissue is described. The method comprises providing a tissue having a planar surface, treating the tissue to reduce surface irregularities, and contouring the tissue surface with a predetermined pattern comprising one or a plurality of ridges or depressions. The ridges and depressions are provided to encourage cellular migration in a first direction and discourage cellular migration in a second direction.

The tissue can be reduced in thickness to a range of about 250-500 microns by compressing the tissue or by removing material from the tissue. The contouring can be performed by a laser, preferably a femtosecond laser. The tissue can be at least partially dried or dehydrated before the contouring, such as by using a glycerin-based treatment solution. The tissue can then be packaged in a package that does not contain a liquid storage solution in contact with the biological tissue.

Yet another embodiment comprises a biological tissue for implantation having a surface contoured with a predetermined pattern comprising at least one ridge or depression configured to encourage cellular migration in a first direction and discourage cellular migration in a second direction.

BRIEF DESCRIPTION OF THE DRAWINGS

Illustrative embodiments of the present disclosure are described herein with reference to the accompanying drawings, in which.

Like numerals refer to like parts throughout the several views of the drawings.

DETAILED DESCRIPTION OF THE PREFERRED EMBODIMENTS

Specific, non-limiting embodiments of the present invention will now be described with reference to the drawings.

It should be understood that such embodiments are by way of example only and merely illustrative of but a small number of embodiments within the scope of the present invention. Various changes and modifications obvious to one skilled in the art to which the present invention pertains are deemed to be within the spirit, scope and contemplation of the present invention as further defined in the appended claims.

Described herein are methods for contouring a biological tissue with a predetermined pattern which are aimed at directing cellular migration in a predetermined pattern across a surface of a bioprosthetic implant. Such implants include heart valve leaflets and patches made of a biological tissue, such as a bovine, equine or porcine pericardium. In a preferred embodiment, the biological tissue is treated such that the tissue is thinned (by compression or by removal of tissue material) and/or the tissue surface is smoothed (by compression and/or crosslinking), as described in U.S. Pub. No. 2011/0238167, published Sep. 29, 2011, and U.S. Pat. No. 7,141,064, issued Nov. 28, 2006, the entire contents of each of which are incorporated herein by reference in their entireties. In a preferred embodiment, the biological tissue is thinned to a thickness of about 100-800 microns, preferably about 250-500 microns and most preferably about 100-300 microns.

Figure 1A:
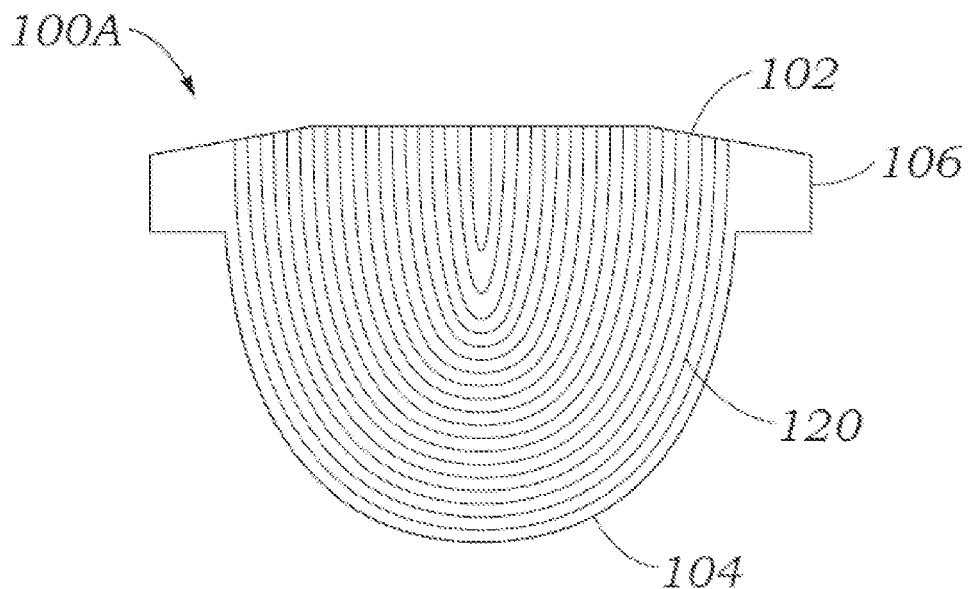
FIG. 1A is a plan view of a bioprosthetic heart valve leaflet having a plurality of parallel grooves.
Figure 1B:
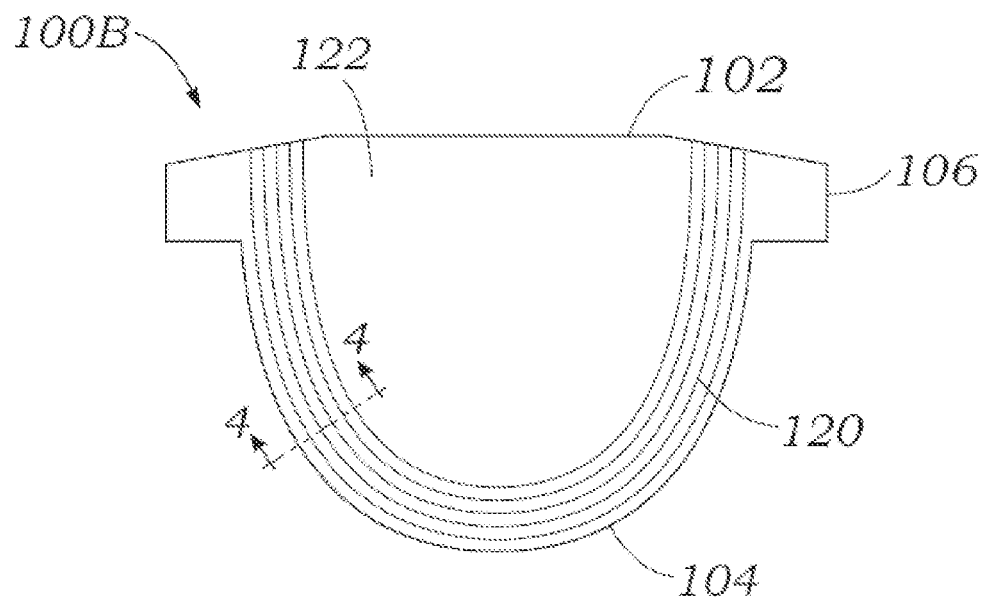
FIG. 1B is a plan view of a bioprosthetic heart valve leaflet having a plurality of parallel grooves disposed only along an area adjacent the cusp edge.

FIGS. 1A-1B depict a bioprosthetic heart valve leaflet 100A having a plurality of parallel grooves 120. The leaflet 100A is depicted herein as comprising an arcuate cusp edge 104, a generally straight free edge 102 opposite the cusp edge 104, and a pair of oppositely-directed tabs 106 at either end of the free edge 102. A plurality of depressions, e.g., grooves, or raised ridges 120 is provided on one side of the leaflet surface and is patterned to follow the shape of the arcuate cusp edge 104. As shown in FIG. 1A, the parallel grooves 120 can be provided on substantially the entire surface of the leaflet 100A or, as shown in FIG. 1B, the parallel grooves can be provided only along the area adjacent the cusp edge 104 of the leaflet 100B. The patterns of parallel grooves 120 depicted in FIGS. 1A-1B are provided to discourage cellular migration in a transverse direction originating from the periphery or central region of the leaflet towards the central region or periphery of the leaflet, respectively.

As used herein, "parallel" refers to two paths that are substantially identical but are offset so as to never intersect. Accordingly, "parallel" is broadly understood to encompass lines, curves and wavy lines that follow the same path but are offset from one another by a constant or variable distance. In a preferred embodiment, adjacent paths are offset by a constant distance.

As used herein, "transversely" refers to a path that intersects the contoured pattern, e.g., grooves or ridges, and is not limited to a particular angle at which the path intersects the contoured pattern.

Certain cells, such as fibroblasts, are believed to have a significant role in the formation and overgrowth of pannus on bioprosthetic heart valves. Fibroblasts are a class of cells that synthesize the extracellular matrix and collagen, the structural framework for animal tissues. Fibroblasts play a critical role in wound healing. Implantation of bioprosthetic heart valves at a valve annulus stimulates fibroblasts to migrate and form a pannus around the heart valve and, more specifically, in the areas surrounding the suture lines of a bioprosthetic heart valve. It is therefore believed that directing the migration of cells (e.g., fibroblasts) responsible for pannus formation will similarly help control the extent and location of pannus growth.

Figure 5:
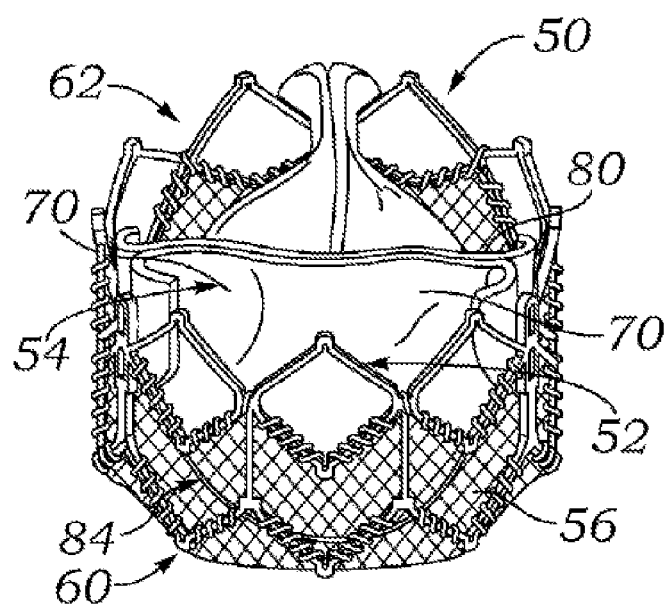
FIG. 5 is a perspective view of a representative embodiment of a prosthetic heart valve that can be made with a biological tissue.

FIG. 5 depicts an embodiment of a bioprosthetic heart valve 50 as generally comprising a structural frame or stent 52, a flexible leaflet structure 54 supported by the frame 52 and a flexible skirt 56 secured to the outer surface of the leaflet structure 54. The valve 50 can be implanted in the annulus of the native aortic valve, but also can be adapted to be implanted in other native valves of the heart or in various other ducts or orifices of the body. Valve 50 has an inflow end 60 and an outflow end 62. Valve 50 and frame 52 are configured to be radially collapsible to a collapsed or crimped state for introduction into the body on a delivery catheter and radially expandable to an expanded state for implanting the valve at a desired location in the body, such as the native aortic valve.

Figure 2:
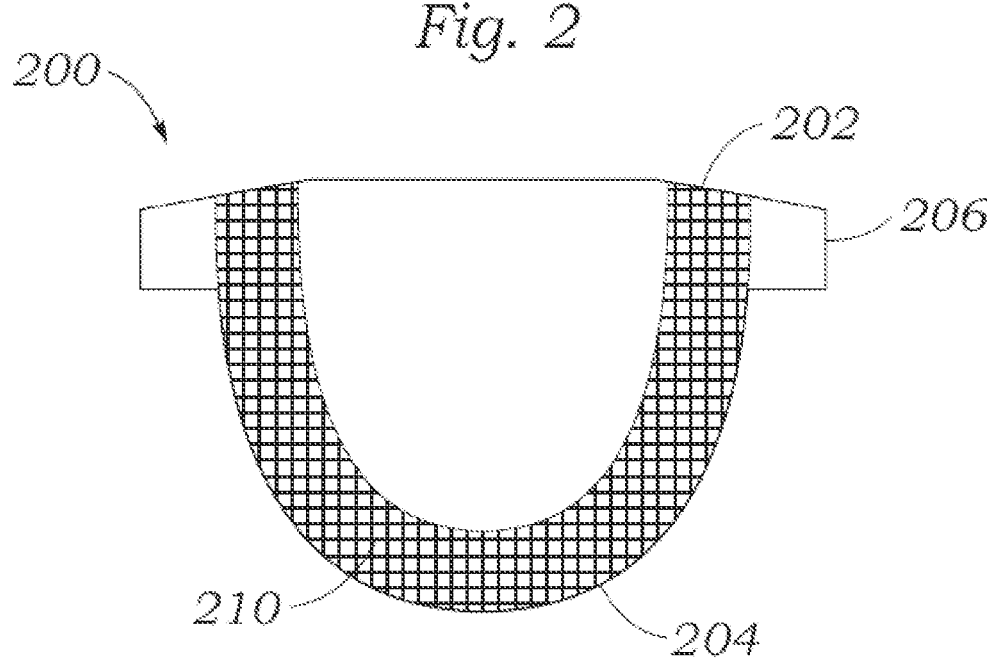
FIG. 2 is a plan view of a bioprosthetic heart valve leaflet having a grid pattern disposed along an area adjacent the cusp edge.
Figure 3:
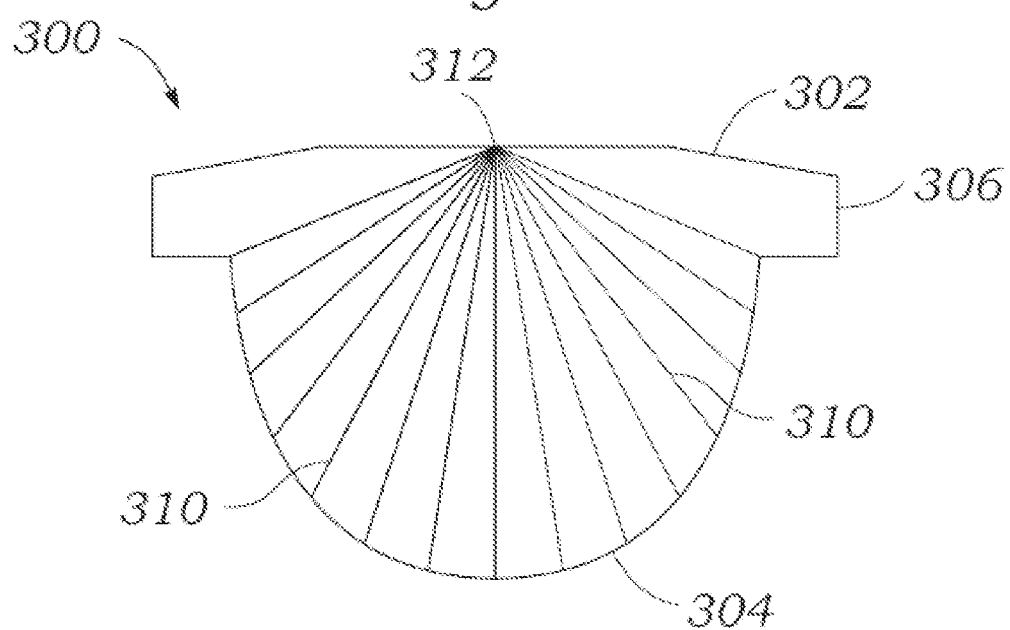
FIG. 3 is a plan view of a bioprosthetic heart valve leaflet having a radial pattern designed to encourage cellular migration on the leaflet surface.
Figure 6:
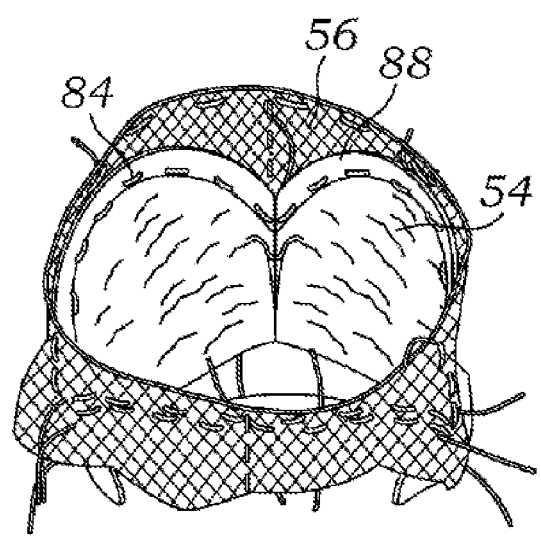
FIG. 6 is a bottom perspective view of a valve leaflet structure connected to a reinforcing skirt so as to form a leaflet assembly.

Leaflet structure 54 desirably comprises three separate connected leaflets 70, which are individually depicted in FIGS. 1-3. The individual leaflets can be arranged together to coapt in a tricuspid arrangement, as best shown in FIGS. 5 and 6. The leaflets 70 attach to one another at their adjacent sides to form commissures 80 of the leaflet structure 54. The leaflets are made of biological tissue, preferably bovine or porcine pericardium, and have a thickness in the range of about 100 to about 800 microns. The curved cusp edge forms a single scallop in the leaflet structure 54 and when secured to two other leaflets 70 to form the leaflet structure 54, the curved cusp edges collectively form a scallop-shaped lower edge of the leaflet structure. A suture line 84 visible on the exterior of the skirt 56 tracks the scalloped shape of the leaflet structure 54. By forming the leaflets with this scalloped geometry, stresses on the leaflets are reduced, which in turn improves durability of the valve 50.

The skirt 56 can be formed, for example, of polyethylene terephthalate (PET) or pericardium, preferably bovine pericardium, ribbon. The leaflet structure 54 attaches to the skirt via a thin PET reinforcing strip 88 or sleeve. The leaflet structure 54 is sandwiched between skirt 56 and the reinforcing strip 88. The suture 84, which secures the reinforcing strip and the leaflet structure 54 to skirt 56 can be any suitable suture, and desirably tracks the curvature of the bottom edge of the leaflet structure 54 as seen on the exterior of the skirt 56 in FIG. 5. The skirt 56 and leaflet structure 54 preferably reside inside the frame 52.

It is believed that pannus growth on bioprosthetic heart valves typically occurs along the suture lines. Thus, with reference to the valve 50 depicted in FIGS. 5 and 6, pannus growth would most likely originate along the suture line 84 which corresponds to the cusp edge 104 of the leaflets 100A and 100B in FIGS. 1A and 1B, typically along the outwardly facing external surface or the circumferential outer peripheral surface of the valve 50 that is in contact with the arterial wall or body lumen. Thus, disposing a plurality of grooves or ridges 120 in a pattern that follows the suture line 84 will discourage or reduce the extent to which pannus growth occurs in a transverse direction to the suture line 84 and reduce the extent to which pannus overgrowth will reach the inflow or outflow orifices or otherwise interfere with the coaptation of the leaflets.

Figure 4:
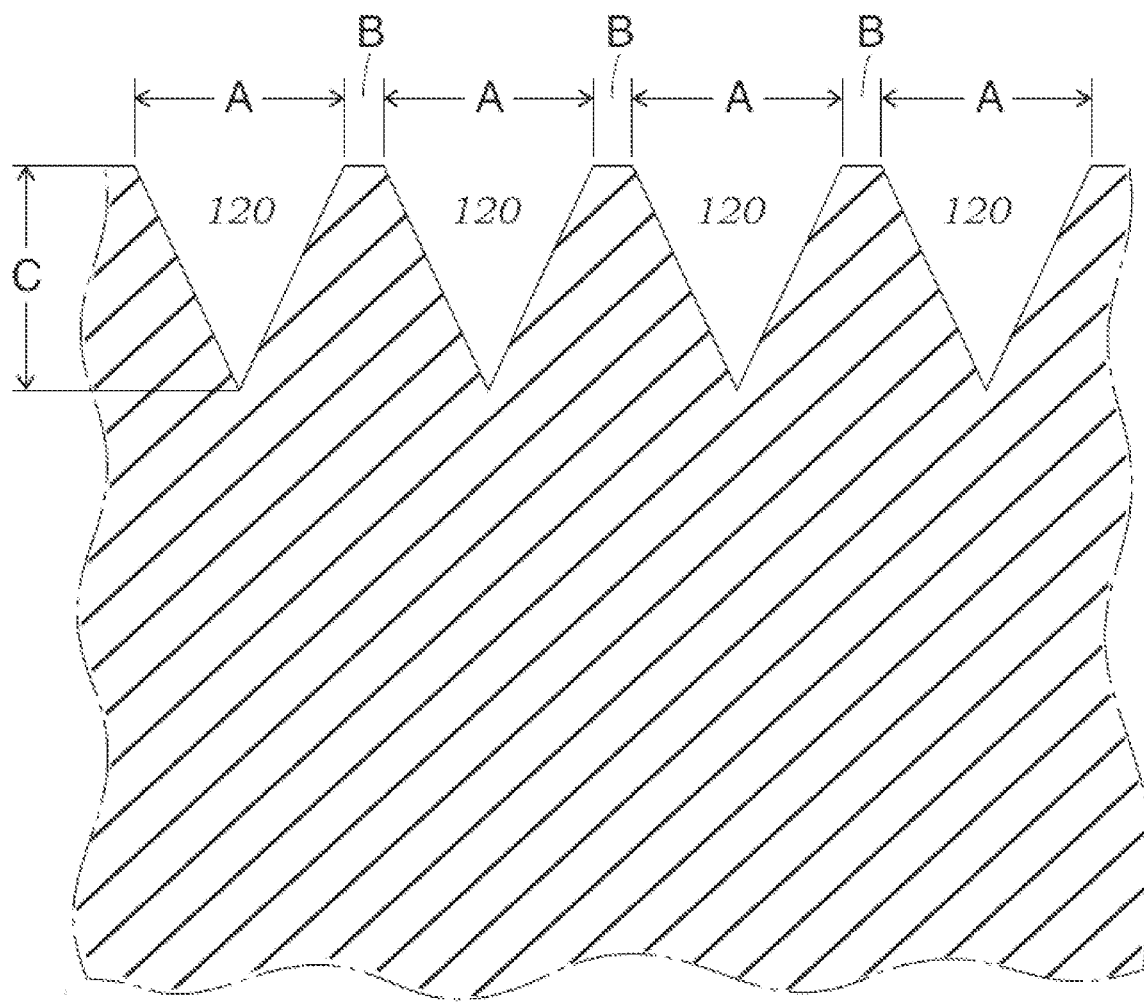
FIG. 4 is a cross-sectional view along 4-4 of FIG. 1B showing the spacing and depth of the respective grooves.

In a preferred embodiment, adjacent grooves or ridges 120 are both dimensioned and offset at a distance that is greater than the average size of a fibroblast or other cell associated with pannus formation. FIG. 4 is a cross-sectional view along 4-4 of FIG. 1B depicting the spacing B between adjacent grooves and the width A and depth C of each groove 120. Fibroblasts are believed to have a size in the range of 10 to 40 microns and more typically from 10 to 20 microns. Thus, in a preferred embodiment, adjacent grooves 120 are offset at a distance B of at least 10 microns, preferably at least 20 microns, more preferably at least 30 microns and most preferably at least 40 microns.

Similarly, one or both of the width A and depth C of the grooves 120 are dimensioned to be at least as large as, if not larger than, the average size of a fibroblast or other cell associated with pannus formation. In a preferred embodiment, one or both of the width A and depth C of each individual groove 120 is at least 10 microns, preferably at least 20 microns, more preferably at least 30 microns and most preferably at least 40 microns.

It is understood that where the leaflets are made from a biological tissue that has been compressed or thinned, that the depth C of the grooves 120 is selected so as to not compromise the strength of the tissue leaflets. In a preferred embodiment, the grooves 120 are provided on only the one side of the leaflet that faces the arterial or cardiac wall when the valve is implanted. The depth C of the grooves 120 preferably does not exceed 25%, preferably 10% and more preferably 5% and most preferably 2% of the average thickness of the leaflet. Thus, for example, for a biological tissue leaflet having a thickness of 250 microns, the depth C of the grooves preferably does not exceed 62.5 microns, preferably 25 microns, more preferably 12.5 microns, and most preferably 5 microns. In the event that a width of less than 5 microns is selected, it is understood that at least one of the other parameters, e.g., the distance B between grooves 120 or the width A of the grooves, is preferably selected to exceed the average cell size of at least 10 microns. The values for A, B and C are selected to sequester or trap the fibroblasts or cells within grooves and/or between adjacent grooves 120. In embodiments where ridges are provided instead of grooves, the consideration with respect to selecting the distance between ridges and height of individual ridges is analogous to the distance between grooves and the depth of the grooves.

FIG. 2 depicts a bioprosthetic heart valve leaflet 200 having a grid pattern 210 disposed along an area adjacent the cusp edge 204 opposite the free edge 202. Here, the grid pattern is provided by two sets of intersecting parallel grooves or ridges which define a plurality of square-shaped cells. In embodiments where grooves are employed, the same considerations as to the distance between adjacent grooves and the width and depth of the grooves as discussed in relation to FIGS. 1A and 1B apply. In embodiments where ridges are employed, however, it is the dimension of the individual cells formed by the intersecting ridges that are operative in preventing cellular migration. The two sets of intersecting parallel ridges need not be at right angles to one another so long as the individual cells themselves are sized or dimensioned to be larger than the average size of a fibroblast or other cell associated with pannus formation. Thus, in a preferred embodiment, the individual cells formed in the tissue have at least a width and a length of at least 10 microns, preferably at least 20 microns, more preferably at least 30 microns and most preferably at least 40 microns.

In certain instances, it is desirable to facilitate or encourage cellular growth across a biological tissue surface. In such instances, FIG. 3 depicts a bioprosthetic heart valve leaflet 300 in which radial grooves 310 are provided as originating from a point 312 on the free edge 302 of the leaflet and extending to the arcuate cusp edge 304. While not depicted in FIG. 3, the radial grooves 310 can also extend into the tab portions 306 in a similar manner. The radial grooves 310 function to direct the cellular migration along their length. Because cellular interaction is desired, the distance between adjacent grooves can be no larger than the average size of fibroblasts or other cells associated with pannus formation as measured from the cusp edge. Thus in a preferred embodiment, this distance is less than 40 microns, preferably less than 30 microns, more preferably less than 20 microns and most preferably less than 10 microns. Smaller distances between radial grooves 310 will permit migration transversely across the radial grooves 310.

While the contouring of the biological tissue has been described and depicted herein with respect to heart valve leaflets, it is understood that such contouring can be performed on any biological tissue that is intended for implantation in the body. For example, the contouring can be provided in connection with biological tissue patches which are used for repair in cardiac and vascular reconstruction, soft tissue deficiency repair, valve leaflet repair, carotid repair, closure of pericardial defects, and suture line reinforcement during general surgical procedures. The dimensions and the location of the contouring would depend upon the intended result: to stimulate cellular migration along a specified area of the tissue or to deter cellular migration and thus tissue formation in specified areas of the tissue. Thus, as explained above, a groove being dimensioned with one or both of a width and depth that is greater than the average diameter of a cell (e.g., 10, 20, 30, or 40 microns) would likely trap the cells, prevent cellular migration transversely across the groove and thus hinder the cells from forming a network necessary to create unwanted tissue formation outside of the groove. Similarly, a ridge can be configured to have a height that effectively prevents cellular migration across the ridge and thus accomplish the same result.

The contouring of the biological tissue valve leaflets to produce grooves or ridges is preferably performed by laser ablation. In one embodiment, the laser is a femtosecond laser. In another embodiment, the laser includes a dual axis scanning lens, 2× beam expansion, 1550 nm wavelength, 31.5 µJ pulse energy on target; 1.6 W average power, 50 Hz repetition rate, 650 fs pulse width (ref); 30 µm laser spot size, elliptical polarization, 112 mm focal length, 400 mm/s coarse milling speed (20 µm fill spacing in cross hatch pattern), and 800 mm/s fine milling speed (20 µm fill spacing in cross hatch pattern).

In a preferred embodiment, the laser is coupled to a guiding device. A substantial amount of technology has been developed for guiding lasers and ablating tissue with great precision. Corneal ablation has been widely practiced and excimer lasers have become common. Reference is made to U.S. Pat. No. 4,840,175, the disclosure of which is incorporated herein by reference in its entirety. Recent work with mode locking lasers having very short pulse lengths in picosecond and femtosecond ranges with reduced heating is also suitable.

Milling machines for precisely guiding lasers are also available. Milling machines employing a laser having the above specifications as the operative tool found to be useful for conveniently processing pericardium membranes have a 2-axis scanning laser head, tissue holders to facilitate loading the work into the machine, an X-Y table to increase working area of the laser and an automatic tissue holder loading mechanism. Mechanisms as described can be employed to selectively ablate a mounted pericardium membrane to generate patterns of different distances and dimensions as described herein. Further description of such mechanisms can be found, for example, in U.S. Pub. No. 2011/0238167, published Sep. 29, 2011, which is incorporated herein by reference in its entirety.

The operation of the milling machine is automated according to input data defining the pattern and the coarseness of the ablation. Typically such machines are arranged to control the depth of the ablation based on the specific height of the surface being worked on. Thus in a preferred embodiment, the tissue is compressed or contoured to a substantially uniform thickness and height. Alternatively, a fixed reference can be used rather than the height of the tissue surface being cut.

Laser ablation to contour the tissue is understood to be advantaged if performed on a substantially dehydrated or dry tissue. This can be accomplished by first fixing the tissue with a glycerin-based treatment. The tissue can first be cross-linked using glutaraldehyde or other suitable fixative. The tissue can also be at least partially dehydrated or dried by other chemical or non-chemical means to permit storage of the contoured tissue in a non-fluid environment. Alternatively, the tissue can be at least partially dehydrated or dried prior to contouring. Methods of treating tissue to at least partially dehydrate or dry the tissue, as compared to its native state, are disclosed in U.S. Pat. No. 8,007,992, issued Aug. 30, 2011 to Edwards Lifesciences, Corp. and U.S. Pat. No. 6,534,004, issued Mar. 18, 2003 to The Cleveland Clinic Foundation, the entire contents of which are incorporated herein by reference in their entireties. The tissue can then be mechanically compressed, cut into leaflets and contoured via laser ablation.

One contemplated sequence for contouring the biological tissue includes first cross-linking the tissue (e.g., bovine or porcine pericardium) with a glutaraldehyde-buffered solution. Next, the tissue can be heat treated using a process such as that disclosed in U.S. Pat. No. 5,931,969 to Carpentier, issued Aug. 3, 1999, the disclosure of which is expressly incorporated herein by reference. Subsequently, the thickness of the tissue can be reduced by compression or by removing tissue material by laser or mechanical means such as by using a dermatome. Finally, the tissue can be treated with a capping and/or reducing agent to mitigate later in vivo calcification, which can also include treating with a glycerol/ethanol solution, as is described for example, in U.S. Pat. No. 7,972,376, issued Jul. 5, 2011 to Edwards Lifesciences Corp., the entire contents of which are incorporated herein by reference in its entirety. The tissue can also be at least partially dehydrated or dried by other chemical or non-chemical means to permit storage of the contoured tissue in a non-fluid environment.

It should be understood that although cross-linking the tissue results in a somewhat easier to handle work piece, the contouring can occur prior to cross-linking as well. Likewise, bulk tissue sheet can be compressed and contoured first before or after fixing, or leaflets can first be cut from the bulk membrane which are then compressed and contoured before or after fixing. Cross-linking the collagenous matrix provides stability prior to implantation to retard degeneration. Further, the fixation process generally operates by blocking reactive molecules on the surface of and within the donor tissue, thereby rendering it substantially non-antigenic and suitable for implantation. Fixing bioprosthetic tissue typically involves contacting the tissue with a cross-linking agent, normally a solution. Exemplary fixing solutions for bioprosthetic tissue such as bovine or porcine pericardium include glutaraldehyde, formaldehyde, other aldehydes, EDC, polyethylene glycol, etc. Other ways to fix tissue exist, including heating, irradiating, etc. The fixing step can help maintain the pericardium in a particular three-dimensional form if undertaken after the membrane is otherwise prepared.

For prosthetic heart valve leaflets, the contoured leaflets are attached to a surrounding heart valve support frame or other such components, and sterilized such as with ethylene oxide. After the tissue has been contoured via laser ablation, calcification nucleation sites (e.g., aldehydes and Schiff bases) can be exposed which creates a propensity for calcification. Repeating the treatment with a capping agent (e.g., ethanolamine) a reducing agent (e.g., sodium borohydride) and a collagen preserving agent (e.g. glycerol) caps the nucleation sites and preserves the collagen integrity following laser ablation. Furthermore, this process will also allow the tissue to be stored in a non-liquid (i.e., non-glutaraldehyde) environment. In other words, the process is especially suitable for dry storage of the tissue.

The invention described and claimed herein is not to be limited in scope by the specific preferred embodiments disclosed herein, as these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

What is claimed is:

1. A method for treating a pericardial tissue, the method comprising:
   treating a pericardial tissue surface to reduce surface irregularities; and
   contouring the pericardial tissue surface with a predetermined pattern comprising one or a plurality of ridges or depressions;
   wherein the one or plurality of ridges or depressions are provided to encourage cellular migration in a first direction and discourage cellular migration in a second direction.

2. The method of claim 1, wherein the pericardial tissue is selected from the group consisting of bovine pericardium, equine pericardium and porcine pericardium.

3. The method of claim 1, wherein the treating comprises thinning the pericardial tissue.

4. The method of claim 3, wherein the pericardial tissue is thinned to a thickness of about 100 to about 800 microns.

5. The method of claim 4, wherein the pericardial tissue is thinned to a thickness of about 250 to about 500 microns.

6. The method of claim 4, wherein the pericardial tissue is thinned to a thickness of about 100 to about 300 microns.

7. The method of claim 3, wherein the thinning is performed by compressing the pericardial tissue, by removing material from the pericardial tissue surface, or both.

8. The method of claim 1, wherein the treating comprises smoothing the pericardial tissue.

9. The method of claim 8, wherein the smoothing comprises compressing the pericardial tissue, crosslinking the pericardial tissue or both.

10. The method of claim 1, wherein the contouring is performed by laser.

11. The method of claim 10, wherein the laser is a femtosecond laser.

12. The method of claim 10, further comprising substantially dehydrating or drying the pericardial tissue before the contouring.

13. The method of claim 10, further comprising treating the pericardial tissue with a glycerin-based treatment before the contouring.

14. The method of claim 10, further comprising treating the pericardial tissue with a fixative.

15. The method of claim 14, wherein the fixative is glutaraldehyde.

16. A method for treating a pericardial tissue, the method comprising:
   cross-linking a pericardial tissue with a fixative;
   exposing the pericardial tissue to a glycerin-based treatment;
   treating the pericardial tissue surface to reduce surface irregularities;
   contouring the pericardial tissue surface with a predetermined pattern comprising one or a plurality of ridges or depressions;
   exposing the pericardial tissue to a capping agent, a reducing agent or both;
   wherein the one or plurality of ridges or depressions are provided to encourage cellular migration in a first direction and discourage cellular migration in a second direction.

17. The method of claim 16, wherein the fixative is glutaraldehyde.

18. The method of claim 16, wherein the cross-linking and the exposing the pericardial tissue to the glycerin-based treatment is performed before the contouring.

19. The method of claim 16, wherein the exposing the tissue to the capping agent, the reducing agent or both is performed after the treating and the contouring steps.

* * * * *